United States Patent
Varshney et al.

(10) Patent No.: US 12,398,330 B2
(45) Date of Patent: Aug. 26, 2025

(54) PROCESS FOR ISOMERIZATION OF $C_5$—$C_7$ HYDROCARBONS IN LIGHT NAPHTHA RANGE

(71) Applicant: Indian Oil Corporation Limited, Mumbai (IN)

(72) Inventors: Pushkar Varshney, Faridabad (IN); Saravanan Subramani, Faridabad (IN); Reshmi Manna, Faridabad (IN); Madhusudan Sau, Faridabad (IN); Gurpreet Kapur Singh, Faridabad (IN); Sankara Sri Venkata Ramakumar, Faridabad (IN)

(73) Assignee: Indian Oil Corporation Limited, Mumbai (IN)

( * ) Notice: Subject to any disclaimer, the term of this patent is extended or adjusted under 35 U.S.C. 154(b) by 609 days.

(21) Appl. No.: 17/663,530

(22) Filed: May 16, 2022

(65) Prior Publication Data

US 2022/0372382 A1 Nov. 24, 2022

(30) Foreign Application Priority Data

May 19, 2021 (IN) .............................. 202121022400

(51) Int. Cl.
*C10G 45/00* (2006.01)
*B01D 3/14* (2006.01)
(Continued)

(52) U.S. Cl.
CPC ............. *C10G 45/58* (2013.01); *B01D 3/143* (2013.01); *C07C 5/00* (2013.01); *C07C 5/22* (2013.01);
(Continued)

(58) Field of Classification Search
CPC ........ C10G 57/00; C10G 45/60; C10G 11/05; C10G 65/14; C10G 45/58; C10G 7/00;
(Continued)

(56) References Cited

U.S. PATENT DOCUMENTS

| 5,994,607 A | 11/1999 | Joly et al. |
| 6,338,791 B1 | 1/2002 | Ragil et al. |

(Continued)

*Primary Examiner* — Prem C Singh
*Assistant Examiner* — Brandi M Doyle
(74) *Attorney, Agent, or Firm* — Workman Nydegger (57) ABSTRACT

The present invention is related to the isomerization process in which a light naphtha stream comprising of paraffinic (mono and single branched), naphthenic and aromatic hydrocarbons in the range of $C_5$-$C_7$ is contacted with the solid catalyst in multiple reaction zones and in presence of hydrogen to produce high octane gasoline predominantly comprising of paraffins (single and di-branched) and naphthenes. The process scheme comprises of more than one isomerization reaction section operating at different temperatures and other operating conditions. The catalyst employed in these reaction sections is a high coordination sulfated mixed metal oxide catalyst which contains at least one noble metal and sulfated zirconia in addition to the other components. The process of the present invention also comprises more than one fractionation section and recycling of a particular stream to the reaction zone for improving the isomerization of light naphtha.

15 Claims, 2 Drawing Sheets

(51) Int. Cl.
*C07C 5/00* (2006.01)
*C07C 5/22* (2006.01)
*C10G 7/00* (2006.01)
*C10G 11/05* (2006.01)
*C10G 45/58* (2006.01)
*C10G 57/00* (2006.01)

(52) U.S. Cl.
CPC ............... *C10G 7/00* (2013.01); *C10G 11/05* (2013.01); *C10G 57/00* (2013.01); *C10G 2300/1044* (2013.01)

(58) Field of Classification Search
CPC ...... C10G 2300/4081; C10G 2300/104; C10G 2300/1044
See application file for complete search history.

(56) References Cited

U.S. PATENT DOCUMENTS

| | | |
|---|---|---|
| 10,113,121 B2 | 10/2018 | Pigourier et al. |
| 10,131,849 B2 | 11/2018 | Prevost et al. |
| 10,414,990 B1 | 9/2019 | Sachan et al. |
| 10,851,315 B1 * | 12/2020 | Lapinski ................ C10G 63/06 |
| 2009/0187054 A1 | 7/2009 | Shecterle |
| 2014/0171706 A1 | 6/2014 | Glover |
| 2016/0311732 A1 | 10/2016 | Banerjee et al. |
| 2018/0282244 A1 | 10/2018 | Kockler |
| 2021/0252495 A1 * | 8/2021 | Sampara ................ B01J 27/053 |

* cited by examiner

PROCESS FOR ISOMERIZATION OF $C_5$—$C_7$ HYDROCARBONS IN LIGHT NAPHTHA RANGE

FIELD OF THE INVENTION

The present invention describes an improved process for isomerization of $C_5$-$C_7$ hydrocarbons in light naphtha stream rich in straight chain paraffinic and naphthenic hydrocarbon components and consists of aromatic components such as benzene, thus producing a gasoline blending stream of high-octane value consisting of paraffins' isomers and naphthenes.

BACKGROUND OF THE INVENTION

With the phase-out of octane enhancing additives such as tetraethyl lead and methyl tert-butyl ether, the focus is on improvement in processes for producing high-octane blending components for gasoline that do not contain aromatics especially benzene, olefins, and sulfur. Isomerization of light naphtha is one such process which is used to convert low octane light straight run naphtha into high octane gasoline blending stream. In this process, the octane number increases by conversion of the straight chain paraffinic and naphthenic hydrocarbons to their respective isomers whose octane is higher than that of their respective straight chain paraffinic and naphthenic hydrocarbon. The feed to the isomerization process may also comprise some of the paraffinic isomers and aromatics. Aromatics like benzene that are present in the light straight run naphtha, are also get saturated during this process.

U.S. Pat. No. 5,994,607 discloses a process of increasing the octane number of petroleum cut containing normal paraffins comprising a fractionating zone and at least two isomerization reaction zone wherein the invention describes the disadvantage of the adsorption process using molecular sieves for separation of the feed stream which is complex and operated in a batch manner.

US2009/0187054A1 discloses a process of isomerization of benzene containing feedstock wherein the benzene present in the feed is saturated in a separate hydrogenation reactor and then fed to two isomerization reactors operating in series.

U.S. Pat. No. 6,338,791B1 provides a process for high octane gasoline pool by hydro-isomerization a feed constituted by $C_5$-$C_8$ cut with Different combinations of hydro-isomerization section consisting of reactor and separation section.

U.S. Pat. No. 10,414,990B1 discloses a process wherein the isomerization of hydrocarbon stream contains at least one of $C_5$ to $C_7$ hydrocarbons. The process involves enhance recovery of hydrogen gas by contacting a portion of hydrotreated feed with the net gas scrubber off-gas stream thus reducing the requirement of make-up hydrogen gas and LPG recovery with and without heat integration.

US2014/0171706A1 provides a method for forming a low-aromatic high-octane product stream from deisohexanizing or deisoheptanizing bottom stream. The invention includes two reaction zones; one isomerization zone and a second upgradation zone wherein the process employs catalyst in both zones which may include chlorided platinum alumina, a crystalline aluminosilicate or zeolite, and a sulfated zirconia.

U.S. Pat. No. 10,113,121B2 describes a process for the production of gasoline by isomerization of light naphtha cut comprising two separation steps in the downstream of the reactor. In this process, first separation step removes the $C_5$ hydrocarbons n-pentane and i-pentane from reactor effluent in two different streams. The heavier hydrocarbons are fed to second separation step where it is separated into three cuts as in standard deisohexanizer column.

U.S. Pat. No. 10,131,849B2 describes a process for the isomerization of light naphtha with a view to forming high octane number gasoline by using thermally integrated de-isopentanizer and de-isohexanizer column to reduce the consumption of high temperature utilities.

US20180282244A1 relates to a method of separating isomerization zone effluent mixture comprising between 5 and 8 carbon atoms into high octane isomerate product streams and low octane streams which may be recycled to the isomerization zone. The separation process makes use of a dividing wall column to efficiently perform the separation of high octane multibranched paraffins from low octane straight chain and single branched paraffins. US20180282244A1 further discloses one or more isomerization reactors, wherein each isomerization reactor may contain different isomerization catalysts and each reactor may operate at different isomerization conditions.

US2016311732A1 relates to processes and apparatuses for isomerizing hydrocarbons. More particularly, relates to processes and apparatuses for separately isomerizing a stream containing $C_5$ and $C_6$ hydrocarbons, and a stream containing $C_7$ hydrocarbons. The process for isomerizing hydrocarbons includes a first hydrocarbon feed that includes hydrocarbons having from 5 to 7 carbon atoms. The first hydrocarbon feed is fractionated to produce a first separated stream that includes hydrocarbons having from 5 to 6 carbon atoms and a second separated stream that includes hydrocarbons having 7 carbon atoms. The isomerization conditions are different for both the streams.

In the above said prior arts, the process of isomerization of light naphtha consisting of n-parrafins, naphthenes, and aromatic compounds usually employed a single reactor configuration or two reactors operating in series with the same type of catalyst in both reactors. As per the process of prior arts, there is cracking of $C_7$ paraffin to less valuable $C_1$-$C_4$ gases, benzene of the hydrocarbon feed saturates in the reactor thus increasing the catalyst bed temperature, and high temperature causes less conversion of n-paraffin to iso-paraffin; and naphthenic crude when processed in isomerization unit hinders the conversion of paraffin and due to the ring opening reaction of naphthenic hydrocarbons to paraffinic hydrocarbon (single and mono-branch), having less octane value, takes place in the isomerization unit which ultimately lowers the octane number of the final product.

SUMMARY OF THE PRESENT INVENTION

Accordingly, the present invention relates to a process for isomerization of C5-C7 hydrocarbons in light naphtha range, the process comprising:
a) feeding a light naphtha hydrocarbon feed (10) to a fractionation column (12) for separating into an i-pentane comprising stream (11), a stream (13) predominantly comprising of n-pentane, n-hexane, mono and di-branched isomers of n-hexane and some methyl cyclopentane, and stream (14) predominantly comprising of methyl cyclopentane, cyclohexane, benzene and $C_7$ paraffinic/naphthenic hydrocarbons;
b) mixing the stream (13) with a recycle stream (29), and hydrogen, and feeding to a first isomerization reactor (16) provided with a mixed metal oxide type catalyst;

c) passing an effluent (17) obtained from the first isomerization reactor (16) through a separator (20) to separate hydrogen (22) and a liquid stream (21) after cooling;

d) feeding the liquid stream (21) to a stabilizer (23) for separating dissolved light gases (24), and bottom stream (25) and sending the stream (25) to a fractionation column (26) to produce a top stream (27), a middle stream (29) and a bottom stream (28);

e) recycling the middle stream (29) to the first isomerization reactor (16);

f) mixing stream (14) from fractionating column (12) with hydrogen and feeding to a second isomerization reactor (30) provided with a mixed metal oxide type catalyst to produce an effluent (32) which is passed through a separator (33) to remove hydrogen (34) and obtain a liquid stream (35) after cooling;

wherein in step a) light naphtha hydrocarbon feed (10) in the fractionation column (12) is optionally separated into only two streams: stream (11a) predominantly comprising of i-pentane, n-pentane, n-hexane, mono and di-branched isomers of n-hexane and some methyl cyclopentane and stream (14) predominantly comprising of methyl cyclopentane, cyclohexane, benzene and $C_7$ paraffinic/naphthenic hydrocarbons and wherein stream (11a) before being feed to the first isomerization reactor (16) is fed to a deisopentanizer (43), along with stream (41) to obtain i-pentane containing stream (44) and stream (13) predominantly comprising of n-pentane, n-hexane, mono branched isomers of n-hexane and some methyl cyclopentane; and wherein the bottom stream (25) in step d) is optionally fed to $C_5/C_6$ splitter (40) for separating into top C5 containing stream (41) predominanently consisting of i-pentane and n-pentane, which is recycled back to the inlet of deisopentanizer (43), and bottom $C_6$ containing stream (42), which is fed to fractionation column (26) to produce a top stream (27a), a middle stream (29) and a bottom stream (28).

In another embodiment, of the present invention, the mixed metal oxide catalyst is a high coordination sulfated mixed metal oxide catalyst, wherein a composition of the catalyst before high temperature treatment, comprising mixtures of:

a) alumina and zirconia in weight ratio of 1:3 to 1:5; and
b) α-amino acids, having molecular weight ≤250;
   wherein the α-amino acids are a combination of α-amino acids with non-polar side chain and basic side chain; and
   wherein the particle size of (a) is less than 37 μm.

In another preferred embodiment of the present invention, the α-amino acid with non-polar side chain is selected from Glycine, Alanine, Valine, Leucine, Isoleucine, Methionine, Proline and Phenylalanine; with molar concentration in the range of 1 to 2M; and wherein the α-amino acid with basic chain is selected from Lysine, Arginine and Histidine, with molar concentration in the range of 2 to 3M.

In another embodiment of the present invention, the hydrogen used in the first isomerization reactor is a combination of make-up hydrogen (19) and recycled hydrogen (22); and the hydrogen used in the second isomerization reactor is a combination of make-up hydrogen (31) and recycled hydrogen (34).

In another embodiment of the present invention, the hydrogen (22) from the separator (20) is passed to a compressor (18) and recycled to the first isomerization reactor (16); and the hydrogen (34) from the separator (33) is passed to a compressor (18') and recycled to the second isomerization reactor (30).

In another embodiment of the present invention, stream (27) consists of predominantly $C_6$ paraffinic di-branched isomers, n-pentane and i-pentane.

In another embodiment of the present invention, stream (27a) consists of $C_6$ paraffinic di-branched isomers.

In another embodiment of the present invention, the isomerate product, obtained after mixing streams (11), (27), (28) and (35), has an improved octane number by 2 to 3 units.

In another embodiment of the present invention, the isomerate product, obtained after mixing streams (44), (27a), (28) and (35), has an improved octane number by of 2 to 3 units.

In another embodiment of the present invention, the stream (28) consists of predominantly cyclohexane and methyl cyclopentane; and the stream (29) consists of n-hexane and mono branched isomers.

In another embodiment, the first isomerization reactor (16) is operated at a temperature in a range of 180-210° C.; and the second isomerization reactor (30) is operated at a temperature in a range of 140-180° C.

In yet another embodiment of the present invention, the liquid stream (35) from the separator (33) consists of cyclohexane, methyl cyclopentane, and other $C_7$ hydrocarbons free from benzene.

OBJECTIVES OF THE PRESENT INVENTION

It is the primary objective of the present invention is to provide an improved process for the production of high octane isomerate using two isomerization reactors employing the same genre of catalyst.

It is the secondary objective of the present invention is to provide high octane isomerate predominantly consists of i-paraffins, napthhenes free from aromatic hydrocarbons like benzene. It is another objective of the invention is to provide two different reaction zones which offer the flexibility of using the high aromatic rich feed.

Another objective of the invention is to provide flexibility to operate two different reaction zones operating at different conditions.

Another objective of the invention is the reduction in cracking of $C_7$ paraffins to less valuable $C_1$-$C_4$ gases, leading to increased liquid yield.

It is yet another objective of the invention is the reduction in the undesired conversion of methyl cyclopentane to n-hexane and subsequently to mono branch $C_6$ paraffins. Since a portion of methyl cyclopentane, present in the feed of the first isomerization reactor, will be converted to cyclohexane and equilibrium between these two naphthene isomers will be maintained, thereby reducing the availability of methyl cyclopentane for undesirable conversion into n-hexane and subsequently to mono branch $C_6$ paraffins.

It is yet another objective of the invention is that the additional conversion of low octane paraffins to high octane branched paraffins. The feed of the first isomerization reactor, operating at high temperature, doesn't contain benzene and thereby no benzene saturation reaction takes place in the reactor which is a highly exothermic reaction. Thus, there is no possibility of excessive temperature rise, which usually happens with feedstock containing benzene. This favors the formation of high octane branched paraffin isomers due to favorable equilibrium at lower temperature.

It is yet another objective of the invention is the production of high octane isomerate. Low operating temperature in the second isomerization reactor inhibits the conversion of methyl cyclopentane (having high octane number) to n-hexane and subsequently to mono branch $C_6$ paraffins (low octane number). This methyl cyclopentane is either present in the reactor feed or produced through isomerization of cyclohexane. This leads to a net increase in product octane number.

It is yet another objective of the invention is the conversion of cyclohexane to methyl cyclopentane in the second isomerization reactor operating in the temperature range of 140-180° C. At higher temperatures, the conversion of cyclohexane to methyl cyclopentane is more favoured. Aromatic components present in the feed stock e.g., benzene will saturate in the second isomerization reactor operating at a lower temperature. Since, the benzene saturation is highly exothermic reaction, thereby increasing the reactor bed temperature required for isomerization of cyclohexane to methyl cyclopentane within the operating limit of the second isomerization reactor. This leads to an increase in octane number.

It is yet another objective of the invention is the enhanced life of the catalyst. It is well known that $C_{7+}$ components present in the isomerization feed is a precursor for coke formation and high temperature favours coke formation. The coke formation also reduces in the first isomerization reactor operating at high temperature in the range of 180° C.-210° C. due to the absence of $C_7$ hydrocarbons in the feed thereby enhancing the catalyst life.

DETAILED DESCRIPTION OF THE INVENTION

For promoting an understanding of the principles of the present disclosure, reference will now be made to the specific embodiments of the present invention further illustrated in the drawings and specific language will be used to describe the same. The foregoing general description and the following detailed description are explanatory of the present disclosure and are not intended to be restrictive thereof. It will nevertheless be understood that no limitation of the scope of the present disclosure is thereby intended, such alterations and further modifications in the illustrated composition, and such further applications of the principles of the present disclosure as illustrated herein being contemplated as would normally occur to one skilled in the art to which the present disclosure relates. Unless otherwise defined, all technical and scientific terms used herein have the same meaning as commonly understood by one of ordinarily skilled in the art to which this present disclosure belongs. The methods, and examples provided herein are illustrative only and not intended to be limiting.

In the present invention, the light naphtha hydrocarbon feed is first separated by fractionation column into three streams; wherein the first stream of hydrocarbon predominantly consists of i-pentane; second stream of hydrocarbons consist of n-pentane, n-hexane and its isomers, and some methyl cyclopentane; and third stream consist of naphthenes mainly cyclohexane and methyl cyclopentane, benzene, and other heavier $C_7$ hydrocarbons. The first stream of hydrocarbon is directly blended with isomerate, the final product from this process. The second stream is fed to the first isomerization reactor employing high coordination sulfated mixed metal oxide catalyst operated at high temperature in the range of 180-210° C. after the addition of hydrogen. The third stream is fed to the second isomerization reactor operated at low temperature also employing high coordination sulfated mixed metal oxide catalyst operated at low temperature in the range of 140-180° C. after addition of hydrogen.

In another preferred embodiment of the present invention, the light naphtha hydrocarbon feed stream is separated by fractionation column into two streams; the first stream predominantly consists of i-pentane, n-pentane, n-hexane, mono and di-branched isomers of n-hexane, and some methyl cyclopentane; and the second stream predominantly consists of methylcyclopentane, cyclohexane, benzene and $C_7$ paraffinic/naphthenic hydrocarbons. There may be some component overlap between these streams, which is frequent when fractionation is used to separate components.

In an embodiment of the present invention, there is a reduction in the undesired conversion of methyl cyclopentane to n-hexane and subsequently to mono branch $C_6$ paraffins, since a portion of methyl cyclopentane, present in the feed of the first isomerization reactor, will be converted to cyclohexane and equilibrium between these two naphthene isomers will be maintained, thereby reducing the availability of methyl cyclopentane for undesirable conversion into n-hexane.

In another embodiment of the present invention, additional conversion of low octane paraffins to high octane branched paraffins. The feed of the first isomerization reactor, operating at high temperature, doesn't contain benzene and thereby no benzene saturation reaction takes place in the reactor which is a highly exothermic reaction. Thus, there is no possibility of excessive temperature rise which usually happens with feedstock containing benzene. Thus, favoring the formation of paraffin isomers due to favourable equilibrium at lower temperature.

In another preferred embodiment, the present process produces high octane isomerate, as the low operating temperature in the second isomerization reactor inhibits the conversion of methyl cyclopentane (having high octane number) to n-hexane and subsequently to mono branch C6 paraffins (low octane number). This methyl cyclopentane is either present in the feed of the second isomerization reactor or formed through isomerization of cyclohexane. This leads to increase in product octane number.

In another embodiment of the present invention, aromatic components present in the feed of the second isomerization reactor e.g., benzene saturates in the second reactor, thereby increasing the reactor bed temperature required for isomerization of cyclohexane to methyl cyclopentane. This contributes to an increase in octane number.

In another embodiment of the present invention, the coke formation reduces in the first isomerization reactor operating at high temperature due to the absence of $C_7$ hydrocarbons in the feed thereby enhancing the catalyst life.

In yet another embodiment of the present invention, a high coordination sulfated mixed metal oxide catalyst, wherein a composition of the catalyst before high temperature treatment, comprising mixtures of:
a) alumina and zirconia in weight ratio of 1:3 to 1:5; and
b) α-amino acids, having molecular weight ≤250;
wherein the α-amino acids are a combination of α-amino acids with non-polar side chain and basic side chain.

In another preferred embodiment of the present invention, particle size of (a) is less than 37 μm.

In another preferred embodiment of the present invention, the α-amino acid with non-polar side chain is selected from Glycine, Alanine, Valine, Leucine, Isoleucine, Methionine, Proline and Phenylalanine; with molar concentration in the range of 1 to 2M.

In another preferred embodiment of the present invention, the α-amino acid with basic chain is selected from Lysine, Arginine and Histidine, with molar concentration in the range of 2 to 3M.

Process Description

Figure 1:
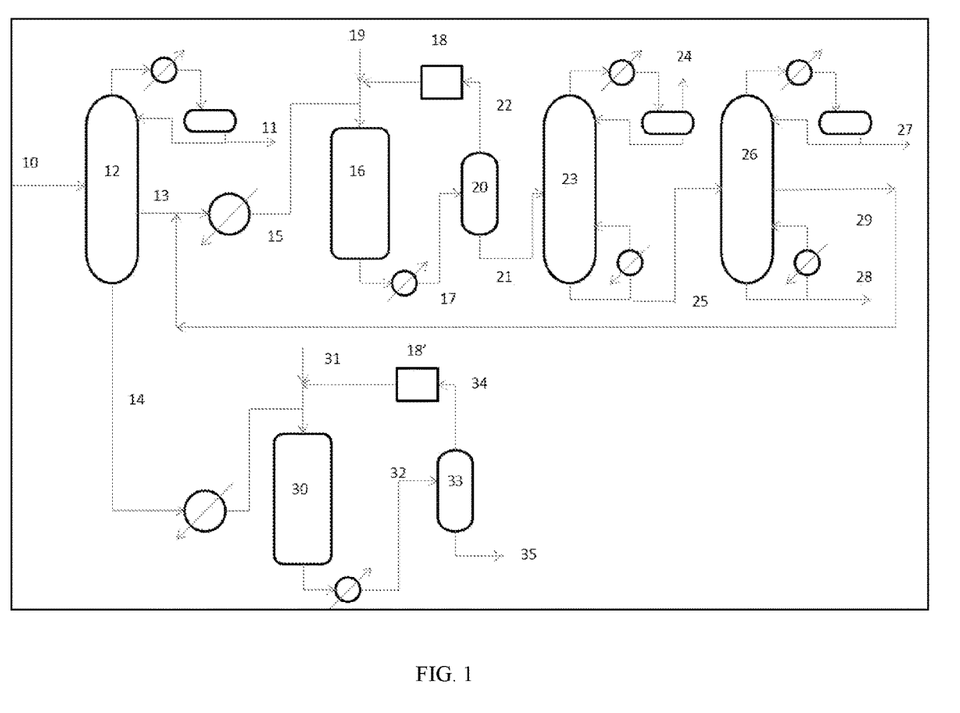
FIG. 1: is a diagrammatic representation of scheme 1 of the present invention.

The process scheme of the present invention is shown in FIG. 1. As per the process scheme as depicted in FIG. 1, the light naphtha hydrocarbon feed stream (10) fed to fractionation column (12) is separated into three streams; stream (11) predominantly consists of i-pentane; stream (13) predominantly consists of n-pentane, n-hexane, mono & di-branched isomers of n-hexane, and some methyl cyclopentane; stream (14) predominantly consists of methyl cyclopentane, cyclohexane, benzene and $C_7$ paraffinic/naphthenic hydrocarbons. There is a possibility of slight overlap of components among these streams, which is common in separation of components using fractionation. Stream (11) is used for blending in the product isomerate. The stream (13) after mixing with recycle stream (29) and hydrogen (make up, 19, and recycle, 22) is fed to first isomerization reactor (16) operating at high temperature usually in the range of 180-210° C. Hydrogen is removed from the reactor effluent (17) through separator (20) after cooling. The liquid stream (21) from the separator is fed to stabilizer (23) to remove dissolved light gases which are removed from top (24). The bottom stream (25) from stabilizer is fed to fractionation column (26). The top stream (27) from the column predominantly consists of di-branched isomers along with $C_5$ hydrocarbons both n-pentane and i-pentane, having high octane number and used for blending in the product isomerate. The middle stream (29) predominantly consists of n-hexane and its mono branched isomers, having low octane number is recycled back to first isomerization reactor for further conversion. The bottom stream (28) predominantly consists of cyclohexane and methyl cyclopentane, along with other heavier components is used for blending in the product isomerate. The bottom stream (14) from fractionating column (12) which consists of predominantly benzene, methyl cyclopentane, cyclohexane and heavier $C_7$ hydrocarbons is fed to second isomerization reactor (30) operating at lower temperature in the range of 140-180° C. after contacting with hydrogen (make up, 31, and recycle, 34). The reactor effluent (32) is passed through separator (33) to remove hydrogen after cooling. The liquid stream (35) from the separator (33) consists of naphthenic hydrocarbon, predominantly cyclohexane and methyl cyclopentane, and other $C_7$ hydrocarbons free from benzene. Since very less cracking will takes place at a lower temperature in the reaction zone, stream (35) is directly used for blending in the product isomerate. Further, instead of two separate compressors (18 and 18') only one compressor can be used with the distribution of the hydrogen stream in both reactors as per the requirement.

Figure 2:
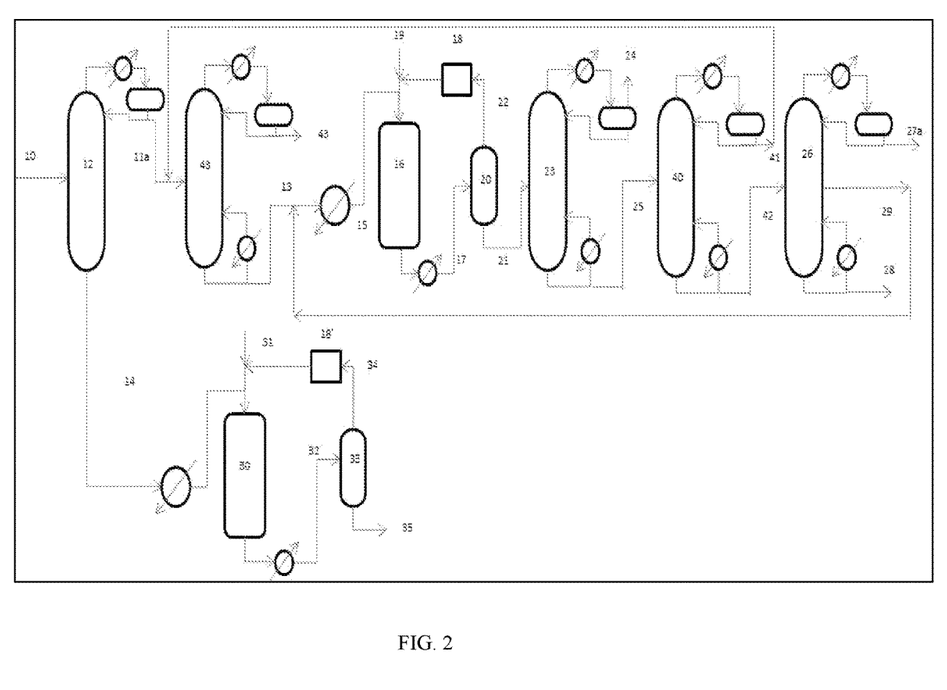
FIG. 2: is a diagrammatic representation of scheme 2 of the present invention.

The process scheme of the present invention as per the second embodiment is shown in FIG. 2. The light naphtha hydrocarbon feed stream (10) is fed to fractionation column (12) is separated into two streams; stream (11a) predominantly consists of i-pentane, n-pentane, n-hexane, mono and di-branched isomers of n-hexane, and some methyl cyclopentane; and stream (14) predominantly consists of methylcyclopentane, cyclohexane, benzene and $C_7$ paraffinic/naphthenic hydrocarbons. There may be some component overlap between these streams, which is frequent when fractionation is used to separate components. The stream 11a is fed to another fractionating column, deisopentanizer (43), after mixing with stream (41) to remove the i-pentane from the top stream (44). Stream (44) is used for blending in the product isomerate. The bottom stream (13) consists of other components predominantly normal paraffins in the range of $C_5$ and $C_6$ alongwith the other components. The stream 13 after mixing with recycle stream (29) and hydrogen (make up, 19, and recycle, 22) is fed to first isomerization reactor (16) operating at high temperature usually in the range of 180-210° C. Hydrogen is removed from the reactor effluent (17) through a separator (20) after cooling. The liquid stream (21) from the separator is fed to stabilizer (23) to remove dissolved light gases which are removed from top (24). The bottom stream (25) from stabilizer is fed to fractionation column, $C_5/C_6$ splitter, (40). The top stream (41) of this column is recycled back to the inlet of deisopentanizer (43). This stream consists $C_5$ components i.e. predominantly i-pentane and n-pentane. The bottom stream (42) of this column consists of $C_6$ and heavier components. This bottom stream is fed to fractionation column (26). The top stream (27a) from the column predominantly consists of C6 paraffinic di-branched isomers, having high octane number and used for blending in the product isomerate. The middle stream (29) consists of n-hexane and its' mono branched isomers, having low octane number is recycled back to first isomerization reactor for further conversion. The bottom stream (28) predominantly consists of cyclohexane, and methyl cyclopentane along with other heavier components is used for blending in the product isomerate. The bottom stream (14) from fractionating column (12) which consists of predominantly methylcyclopentane, benzene, cyclohexane and heavier $C_7$ hydrocarbons is fed to second isomerization reactor (30) operating at lower temperature in the range of 140-180° C. after contacting with hydrogen (make up, 31, and recycle, 34). The reactor effluent (32) is passed through a separator (33) to remove hydrogen after cooling. The liquid stream (35) from the separator (33) consists of naphthenic hydrocarbon, predominantly cyclohexane and methyl cyclopentane, and other $C_7$ hydrocarbons free from benzene. Since very less cracking will takes place at lower temperature in the reaction zone, stream (35) is directly used for blending in the product isomerate. Further, instead of two separate compressors (18 and 18') only one compressor can be used with the distribution of the hydrogen stream in both reactors as per the requirement.

In the above embodiments, both first and second isomerizartion reactors may operate at the same or different process conditions such as pressure in the range of 15-35 bar, weight hour space velocity in the range of 1.25-4.0 $h^{-1}$ and hydrogen to hydrocarbon ratio in the range of 0.5-4.0 mol/mol.

Following examples, as given below, will substantiate the performance of the reactors using a high coordination sulfated mixed metal oxide catalyst at different temperatures as proposed in the scheme. The catalyst used in the below examples is prepared as per the method given in Indian Patent Application no. 202021007171, details of which are incorporated herein by way of reference.

Example 1

Feed Composition:

| Component | Wt % |
| --- | --- |
| Cyclopentane | 1.20 |
| i-Pentane | 0.54 |
| n-Pentane | 6.72 |
| 22DMB | 2.70 |
| 23DMB | 5.92 |
| n-Hexane | 20.41 |
| 2MP | 25.19 |
| 3MP | 17.68 |
| Benzene | 2.22 |
| Cyclohexane | 3.97 |
| Methyl cyclopentane | 11.14 |
| C7+ | 2.32 |

| Temperature, °C. | Pressure, bar | WHSV, h$^{-1}$ | n-pentane conversion, wt % | n-hexane conversion, wt % | ΔRON (Product − Feed) |
| --- | --- | --- | --- | --- | --- |
| 200 | 20 | 1.5 | 53.6 | 41.8 | 9.1 |
| 200 | 20 | 2.0 | 48.7 | 40.4 | 8.4 |

This example shows that the activity of the high coordination sulfated mixed metal oxide catalyst towards the conversion of n-pentane and n-hexane, and RON improvement in a once-through operation at 200° C. which is the operating temperature of the first isomerization reactor using light naphtha stream.

Example 2

Feed Composition:

| Component | Wt % |
| --- | --- |
| Cyclopentane | 1.21 |
| i-Pentane | 0.53 |
| n-Pentane | 6.69 |
| 22DMB | 2.69 |
| 23DMB | 5.92 |
| n-Hexane | 20.44 |
| 2MP | 25.15 |
| 3MP | 17.68 |
| Benzene | 2.24 |
| Cyclohexane | 3.96 |
| Methyl cyclopentane | 11.16 |
| C7+ | 2.34 |

| Temperature, °C. | Pressure, bar | WHSV, h-1 | Benzene conversion, wt % | n-pentane conversion, wt % | n-hexane conversion, wt % |
| --- | --- | --- | --- | --- | --- |
| 140 | 32 | 1.5 | 100 | 3.22 | 3.06 |
| 180 | 20 | 2.0 | 100 | 19.6 | 29.2 |

The experiments were conducted at different temperatures in the range of 140-180° C. at H$_2$/HC ratio of 2.5 mol/mol using the light naphtha stream as per the above mentioned composition. This example shows the activity of the high coordination sulfated mixed metal oxide catalyst towards the benzene saturation takes place in the second isomerization reactor operating in the temperature range of 140-180° C. at different process conditions using light naphtha stream. The above results indicate complete saturation of benzene present in the light naphtha stream and substantially lower activity in terms of n-pentane and n-hexane conversion in the temperature range of 140-180° C.

Example 3

Feed Composition:

| Component | Wt % |
| --- | --- |
| 2MP | 19.5 |
| Cyclohexane | 80.5 |

| Temperature, °C. | Pressure, bar | WHSV, h-1 | Gas yield, wt % | (Methyl cylopentane + Cyclohexane) in the product, wt % | ΔRON (Product − Feed) |
| --- | --- | --- | --- | --- | --- |
| 160 | 20 | 2.6 | 0.11 | 77.86 | 0.35 |
| 180 | 20 | 2.6 | 0.45 | 75.55 | 0.09 |
| 200 | 20 | 2.6 | 1.36 | 70.70 | −0.40 |

The experiments were conducted at different temperatures in the range of 160-200° C. at H$_2$/HC ratio of 3.0 mol/mol using the synthetic feed as per the above mentioned composition. The above example shows that if the feed predominantly contains naphthenic hydrocarbons then the gas yield (C$_1$-C$_4$) increases with an increase in temperature which consequentially decreases the isomerate yield. The experimental results further indicate the decrease in sum of methylcyclopentane and cyclohexane, in the product with the increase in the temperature which results in a decrease in the product RON. These results substantiate that the conversion of methylcyclopentane, formed through isomerization of cyclohexane in the feed, to n-hexane and subsequently to mono branch paraffins increases with an increase in the temperature.

Example 4

Feed Composition:

| Component | Wt % |
|---|---|
| Benzene | 11 |
| Cyclohexane | 67 |
| n-heptane | 22 |

| Temperature, °C. | Pressure, bar | WHSV, h$^{-1}$ | Gas yield (C$_1$-C$_4$), wt % |
|---|---|---|---|
| 160 | 20 | 1.5 | 0.29 |
| 170 | 20 | 1.5 | 0.58 |
| 200 | 20 | 1.5 | 9.36 |

The experiments were conducted at different temperatures in the range of 160-200° C. at H$_2$/HC ratio of 2.5 mol/mol using the synthetic feed as per the above mentioned composition. The experimental results show that if the feed contains a substantial amount of benzene, C$_7$ and naphthenic hydrocarbons then the gas yield (C1-C4) formed due to undesired cracking reactions substantially increases with increase in temperature specifically in the operating temperature of first isomerization reactor which in-turn decreases the isomerate yield. These results corroborate that it is advantageous to process the feed containing benzene, naphthenic and C$_7$ hydrocarbons at a lower temperature i.e. operating temperature of the second isomerization reactor as per the present invention to avoid the cracking reaction.

Example 5

| | Composition, Wt % | |
|---|---|---|
| Component | Feed X | Feed Y |
| n-pentane | 80 | 89 |
| Cyclohexane | 10 | 0 |
| Methyl cyclopentane | 10 | 11 |

| | Feed X | Feed Y |
|---|---|---|
| paraffinic-C6 (n-hexane + mono branch isomers) in the product, wt % | 4.39 | 3.25 |
| ΔRON (Product − Feed) | 11.92 | 14.12 |

The experiments were conducted at 200° C., 20 bar using the synthetic feed in a mixture of n-hexane and methylcyclopentane with and without cyclohexane at WHSV of 1.5 h$^{-1}$ and H$_2$/HC ratio of 2.6 mol/mol. From the experimental results, a reduction of 1.14 wt % in the formation of n-hexane and mono branch C$_6$ paraffins in the product and an increase in the ΔRON of 2.2 units are observed when using feed without cyclohexane. This example shows the reduction in the formation of n-hexane and subsequently to mono branch C$_6$ paraffins from methyl cyclopentane in the feed without cyclohexane in comparison with the feed with cyclohexane as anticipated in the present invention where the feed of the first isomerization reactor does not contain cyclohexane.

Example 6

Feed Composition:

| | Composition, Wt % | | |
|---|---|---|---|
| Component | Feed A | Feed B | Feed C |
| n-Pentane | 25 | 45.5 | 0 |
| n-Hexane | 30 | 54.5 | 0 |
| Benzene | 5 | 0 | 11 |
| Cyclohexane | 30 | 0 | 67 |
| C7+ | 10 | 0 | 22 |

| | Product RON |
|---|---|
| Conventional process scheme | |
| Experimental results using Feed-A (at 200° C.) | 79.71 |
| Process scheme as per the present invention | |
| Experimental results using Feed-B as per first isomerization reactor conditions (at 200° C.) | 84.80 |
| Experimental results using Feed-C as per second isomerization reactor conditions (at 170° C.) | 80.46 |
| Combined product after blending product obtained after processing Feed-B and C | 82.91 |
| Benefit in terms of RON improvement of new process scheme over the conventional scheme | 3.20 |

This example shows the once-through experimental results at 20 bar, WHSV of 1.5 h−1 and H$_2$/HC ratio of 2.6 mol/mol with the synthetic feed using a single reaction zone operating at high temperature as per the conventional process scheme and the two reaction zones operating at different process conditions as per the present invention. Feed-A which is a mixture of paraffinic, napthenic and aromatic hydrocarbons in the light naphtha range is used in experiments to estimate once through RON as per the conventional scheme. While, Feed-B and Feed-C, which are representative of the cuts obtained after the separation of Feed-A, are used in the experiments with two reactions zone as per the present invention. The experimental results indicate an increase in the RON in the final product as compared to the conventional process.

Advantages of the Present Invention:

An improved process for the production of high octane isomerate using two reactors employing the same genre of catalyst.

Production of high octane isomerate consisting of i-paraffins and naphthenes free from aromatic hydrocarbons like benzene.

Reduction in cracking of C$_7$ paraffins to less valuable C$_1$-C$_4$ gases, leading to increased liquid yield; and reduction in the undesired conversion of methyl cyclopentane to n-hexane.

Conversion of low octane paraffins to high octane branched paraffins.

What is claimed is:

1. A process for isomerization of C$_5$-C$_7$ hydrocarbons in light naphtha range, the process consisting of:
   a) feeding a light naphtha hydrocarbon feed to a first fractionation column for separating into a first stream, a second stream, and a third stream, wherein the first stream consists of i-pentane, the second stream consists of n-pentane, n-hexane, mono and di-branched isomers of n-hexane and methyl cyclopentane, and the third stream consists of methyl cyclopentane, cyclohexane, benzene and $C_7$ paraffinic/naphthenic hydrocarbons;

b) mixing the second stream with a recycled middle stream from a second fractionation column, and hydrogen, and feeding to a first isomerization reactor provided with a mixed metal oxide type catalyst;

c) passing a first effluent obtained from the first isomerization reactor through a first separator to separate hydrogen and a first liquid stream after cooling;

d) feeding the first liquid stream to a stabilizer for separating dissolved light gases, and a first bottom stream and sending the first bottom stream to the second fractionation column to produce a top stream, the middle stream and a second bottom stream; and e) mixing the third stream from the first fractionating column with hydrogen and feeding to a second isomerization reactor provided with a mixed metal oxide type catalyst to produce a second effluent which is passed through a second separator to remove hydrogen and obtain a second liquid stream after cooling, wherein an isomer product of $C_5$-$C_7$ hydrocarbons in light naphtha range is a mixture of the first stream, the top stream of the second fractionation column, the second bottom stream of the second fractionation column, and the second liquid stream, wherein the hydrogen used in the first isomerization reactor is a combination of a first make-up hydrogen and recycled hydrogen from the first separator, wherein the hydrogen used in the second isomerization reactor is a combination of a second make-up hydrogen and recycled hydrogen from the second separator, wherein the hydrogen from the first separator is passed to a first compressor and recycled to the first isomerization reactor, and wherein the hydrogen from the second separator is passed to a second compressor and recycled to the second isomerization reactor.

2. The process as claimed in claim 1, wherein the mixed metal oxide catalyst provided in the first isomerisation reactor and in the second isomerisation reactor is a high coordination sulfated mixed metal oxide catalyst, wherein a composition of the catalyst before high temperature treatment, comprises mixtures of:
   a) alumina and zirconia in weight ratio of 1:3 to 1:5; and
   b) α-amino acids, having molecular weight≤250,
wherein the α-amino acids are a combination of α-amino acids with a non-polar side chain and a basic side chain; and wherein the particle size of (a) is less than 37 μm.

3. The process as claimed in claim 2, wherein the α-amino acid with the non-polar side chain is selected from the group consisting of Glycine, Alanine, Valine, Leucine, Isoleucine, Methionine, Proline and Phenylalanine with a molar concentration in a range of 1 to 2M; and
   wherein the α-amino acid with the basic chain is selected from the group consisting of Lysine, Arginine and Histidine, with a molar concentration in a range of 2 to 3M.

4. The process as claimed in claim 1, wherein the top stream of the second fractionation column consists of $C_6$ paraffinic di-branched isomers, n-pentane, and i-pentane.

5. The process as claimed in claim 1, wherein the isomerate product has an improved octane number by 2 to 3 units.

6. The process as claimed in claim 1, wherein the second bottom stream predominantly consists of cyclohexane and methyl cyclopentane.

7. The process as claimed in claim 1, wherein the middle stream consists of n-hexane and mono branched isomers.

8. The process as claimed in claim 1, wherein the first isomerization reactor is operated at a temperature in a range of 180-210° C.; and wherein the second isomerization reactor is operated at a temperature in a range of 140-180° C.

9. The process as claimed in claim 1, wherein the second liquid stream from the second separator consists of cyclohexane, methyl cyclopentane, and $C_7$ hydrocarbons free from benzene.

10. The process as claimed in claim 9, wherein the third top stream consists of predominantly $C_6$ paraffinic di-branched isomers.

11. The process as claimed in claim 9, wherein the isomerate product has an improved octane number by 2 to 3 units.

12. The process as claimed in claim 9, wherein the first isomerization reactor is operated at a temperature in a range of 180-210° C.; and wherein the second isomerization reactor is operated at a temperature in a range of 140-180° C.

13. The process as claimed in claim 12, wherein the α-amino acid with the non-polar side chain is selected from the group consisting of Glycine, Alanine, Valine, Leucine, Isoleucine, Methionine, Proline and Phenylalanine with a molar concentration in a range of 1 to 2M; and
   wherein the α-amino acid with the basic chain is selected from the group consisting of Lysine, Arginine and Histidine, with a molar concentration in a range of 2 to 3M.

14. The process as claimed in claim 9, wherein the mixed metal oxide catalyst provided in the first isomerisation reactor and in the second isomerisation reactor is a high coordination sulfated mixed metal oxide catalyst, wherein a composition of the catalyst before high temperature treatment, comprises mixtures of:
   a) alumina and zirconia in weight ratio of 1:3 to 1:5; and
   b) α-amino acids, having molecular weight≤250,
wherein the α-amino acids are a combination of α-amino acids with a non-polar side chain and a basic side chain; and wherein the particle size of (a) is less than 37 μm.

15. A process for isomerization of $C_5$-$C_7$ hydrocarbons in light naphtha range, the process consisting of:
   a) feeding a light naphtha hydrocarbon feed to a first fractionation column for separating into a first stream consisting of i-pentane, n-pentane, n-hexane, mono and di-branched isomers of n-hexane and methyl cyclopentane, and a second stream consisting of methylcyclopentane, cyclohexane, benzene and $C_7$ paraffinic/naphthenic hydrocarbons;
   b) mixing the first stream with a recycled second top stream from a $C_5$/$C_6$ splitter and feeding to a deisopentanizer to obtain a first top stream and a first bottom stream, wherein the first top stream consists of i-pentane;
   c) mixing the first bottom stream with a recycled middle stream from a second fractionation column, and hydrogen, and feeding to a first isomerization reactor provided with a mixed metal oxide type catalyst;
   d) passing a first effluent obtained from the first isomerization reactor through a first separator to separate hydrogen and a first liquid stream after cooling;
   e) feeding the first liquid stream to a stabilizer for separating dissolved light gases from a top of the stabilizer, and a second bottom stream and sending the second bottom stream to the $C_5$/$C_6$ splitter to produce a second top stream, and a third bottom stream;

f) sending the third bottom stream to the second fractionation column to produce a third top stream, the middle stream and a fourth bottom stream;

g) mixing the second stream from the first fractionating column with hydrogen and feeding to a second isomerization reactor provided with a mixed metal oxide type catalyst to produce a second effluent which is passed through a second separator to remove hydrogen and obtain a second liquid stream after cooling, wherein an isomer product of $C_5$-$C_7$ hydrocarbons in light naphtha range is a mixture of first top stream, the third top stream of the second fractionation column, the fourth bottom stream of the second fractionation column, and the second liquid stream.

* * * * *